US005856258A

United States Patent [19]
Marks et al.

[11] Patent Number: 5,856,258
[45] Date of Patent: Jan. 5, 1999

[54] PHENOLATE CONSTRAINED GEOMETRY POLYMERIZATION CATALYST AND METHOD FOR PREPARING

[75] Inventors: Tobin J. Marks, Evanston; You-Xian Chen, Chicago, both of Ill.

[73] Assignee: Northwestern University, Evanston, Ill.

[21] Appl. No.: 950,912

[22] Filed: Oct. 15, 1997

Related U.S. Application Data

[60] Provisional application No. 60/028,412, Oct. 15, 1996.
[51] Int. Cl.[6] .............................. B01J 31/00; C07F 7/00; C07F 7/28; C08F 4/44
[52] U.S. Cl. .................. 502/152; 502/104; 502/103; 502/108; 502/111; 502/117; 502/128; 526/134; 526/943; 556/52
[58] Field of Search ........................ 502/103, 108, 502/111, 117, 128, 152; 526/134, 943; 556/52

[56] References Cited

U.S. PATENT DOCUMENTS

| 5,272,236 | 12/1993 | Lei et al. ............... | 502/152 |
| 5,374,696 | 12/1994 | Rosen et al. ........... | 526/160 |
| 5,446,117 | 8/1995 | Baird et al. ............ | 526/134 |
| 5,495,036 | 2/1996 | Wilson et al. .......... | 556/52 |
| 5,637,660 | 6/1997 | Nagy et al. ............ | 556/52 |

FOREIGN PATENT DOCUMENTS 0 426 637  5/1991  European Pat. Off.

OTHER PUBLICATIONS

Jun Okuda, "Bifunctional Cyclopentadienyl Ligands in Organotrasition Metal Chemistry", Comments Inorg. Chem, 1994, vol. 16, No. 4, pp. 185–205.

Peter Jutzi, Ulrich Siemeling, "Cyclopentadienyl Compounds with Nirtogen Donbors in the Side–Chain", Journal of Roganometallic Chemistry 500, 1995, pp. 175–185.

Adolphus A. H. van der Zeijden and Chris Mettheis, "Syntheseis and Characterization of Monocylopentadienyl Titanium and Ziroconium Complexes Bearing a Chelating (Chiral) Ether Side Chain on the Cp Ring", Organometallicas, 1997, vol. 16, pp. 2651–2658.

Trouve et al., "Sybntheseis of Group 4 Metal Compounds Containing Cyclopentadienyl Ligand with a Pendant Alkoxide Funtion: Moelcula Structure of . . . ", Journal of Organic Chemistry, 1996, vol. 511, pp. 255–262.

Jens Christoffers, Robert G. Bergman, "Stereoselective Synthesis of Chiral Zirconocenses from Doubly Substituted, Donor Functionalized Cyclopentadienes via Helical Chelate Complexes", Angew. Chem. Int. Ed. Engl., 1995, vol. 34, No. 20, pp. 2266–2267.

U. Zucchini et al., J. Organomet. Chem., vol. 26, pp. 357–372, 1971.

R.T. Morrison, R.N. Boyd, "Organic Chemistry", 3rd ed., Allyn and Bacon, Boston, pp. 456–458, 1976.

Primary Examiner—Mark L. Bell
Assistant Examiner—J. Pasterczyk
Attorney, Agent, or Firm—Welsh & Katz, Ltd.

[57]  ABSTRACT

The subject invention involves a method of preparing and the constrained geometry catalyst thereby prepared of the general formula $Ar'R4(O)Ar''R'_4M(CH_2Ph)_2$ where Ar' is a phenyl or naphthyl group; Ar" is a cyclopentadienyl or indenyl group, R and R' are H or alkyl substituents ($C \leq 10$) and M is Ti, Zr or Hf. The synthetic method involves a simple alkane elimination approach which permits a "one-pot" procedure. The catalyst, when combined with a cocatalyst such as $Pb_3C^+B(Ar_3^F)_4BAr_3^F$ or methyl alumoxane where $Ar^F$ is a fluoroaryl group, is an effective catalyst for the polymerization of α-olefins such as ethylene, propylene and styrene.

8 Claims, 1 Drawing Sheet

PHENOLATE CONSTRAINED GEOMETRY POLYMERIZATION CATALYST AND METHOD FOR PREPARING

This invention was made with Government support under Contract No. DE-FG02-86ER13511 awarded by the Department of Energy. The Government has certain rights in this invention.

This is a non-provisional application, from provisional application Ser. No. 60/028,412, filed Oct. 15, 1996.

BACKGROUND OF THE INVENTION

This invention relates to the compositions of matter useful as a catalyst system, to a method for preparing these catalyst systems and to a method for polymerization utilizing the catalyst system.

The use of soluble Ziegler-Natta type catalysts in the polymerization of olefins is well known in the prior art. In general, such systems include a Group IV-B metal compound and a metal or metalloid alkyl cocatalyst, such as aluminum alkyl cocatalyst. More broadly, it may be said to include a mixture of a Group I–III metal alkyl and a transition metal complex from the Group IVB–VB metals, particularly titanium, zirconium, or hafnium with aluminum alkyl cocatalysts.

First generation cocatalyst systems for homogeneous metallocene Ziegler-Natta olefin polymerization, alkylaluminum chlorides ($AlR_2Cl$), exhibit low ethylene polymerization activity levels and negligible propylene polymerization activity. Second generation cocatalyst systems, utilizing methyl aluminoxane (MAO), raise activities by several orders of magnitude. In practice however, a large stoichiometric excess of MAO over catalyst ranging from several hundred to ten thousand must be employed to have good activities and stereoselectivities. Moreover, it has not been possible to isolate characterizable metallocene active species using MAO. The third generation of cocatalyst, $B(C_6F_5)_3$, proves to be far more efficient while utilizing a 1:1 catalyst-cocatalyst ratio. Although active catalyst species generated with $B(C_6F_5)_3$ are isolable and characterizable, the anion $MeB(C_6F_5)_3^-$ formed after $Me^-$ abstraction from metallocene dimethyl complexes is weakly coordinated to the electron-deficient metal center, thus resulting in a decrease of certain catalytic activities. The recently developed $B(C_6F_5)_4^-$ types of non-coordinating anions exhibit some of the highest reported catalytic activities, but such catalysts have proven difficult to obtain in the pure state due to poor thermal stability and poor crystallizability, which is crucial for long-lived catalysts and for understanding the role of true catalytic species in the catalysis for the future catalyst design. Synthetically, it also takes two additional steps to prepare such an anion than for the neutral organo-Lewis acid.

Ligand modifications have played a key role in developing new "single-site" group 4 metallocene catalyst precursors for optimizing polymerization activity as well as polymer properties such as stereoregularity, molecular weight, thermal/rheological characteristics, bulky and polar comonomer incorporation and microstructure. In particular, complexes of bifunctional monocyclopentadienyl ligands having an appended heteroatom donor attracted considerable attention, as exemplified by "constrained geometry catalysts" having the formula $ME_2Si(\eta^5-Me_4C_5)(BuN)MX_2$ (CGCMX$_2$; M=Ti, Zr, Hf; X=Cl, Me, CH$_2$Ph). These catalysts have a covalently attached amide donor ligand which stabilizes the electrophilic metal center electronically, while the short Me$_2$Si<bridging group considerably opens the metal coordination sphere vis-à-vis a conventional metallocene. The result upon activation with a variety of cocatalysts is a new generation of catalysts which, among other features, efficiently produce ultra-low density elastomeric ethylene-octene copolymers.

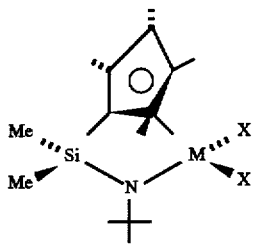

CGCMX$_2$; M = Ti, Zr, Hf; X = Cl, Me, CH$_2$Ph

Given the import of the Cp-appended heteroatom donor groups on the catalytic performance of such complexes, ligand design remains a very active and challenging area of olefin polymerization research and much attention has been paid to the design of new N- and O-containing ligands.

SUMMARY OF THE INVENTION

Accordingly, it is an object of the subject invention to prepare and utilize a new class of olefin polymerization catalytic system.

A further object of the subject invention is a catalytic system which permits better control over molecular weight, molecular distribution, stereoselectivity, and stability.

Another object of the subject invention is a Ziegler-Natta type catalytic system which uses a one-step synthetic approach.

These and other objects are attained by the subject invention whereby in one embodiment, there is a new method of synthesis of a constrained geometry catalyst system, i.e., a convenient "one-pot" synthesis of a new bifunctional mono-Cp ligand containing an appended phenolate group ((TCP)H$_2$) as well as efficient one-step syntheses of the corresponding C$_s$ symmetric Ti and chiral C$_2$-symmetric Zr complexes. This ligand system includes a straight forward and efficient synthetic procedure as well as great intrinsic steric and electronic flexibility introducible via modification of the aryl fragment. Further, this invention teaches the solution and solid state structure, cocatalyst abstraction/activation chemistry and the use of the subject catalytic system, in olefin polymerization with a 2-tetramethylcyclopentadienyl-4-methyl phenolate ligand complex.

CONCISE DESCRIPTION OF THE DRAWINGS

FIG. 1 is a partial ORTEP Figure of the catalytic complex of the subject invention.

DETAILED DESCRIPTION OF THE INVENTION

Figure 1:
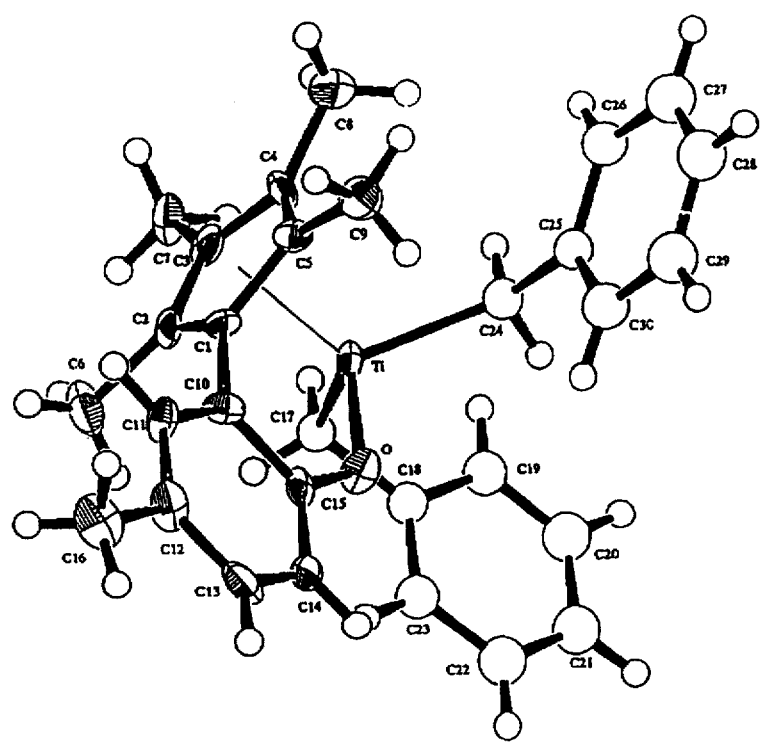

The subject invention involves a method of preparing a constrained geometry catalyst of the general formula $ArR_4(O)Ar"R'_4M(CH_2Ph)_2$ where $Ar'$ is a phenyl or naphthyl group; $Ar"$ is a cyclopentadienyl or indenyl group, R and R' are H or alkyl substituents (C≦10) and M=Ti, Zr or Hf. The synthetic method involves a simple alkane elimination approach which permits a "one-pot" procedure. The catalyst, when combined with a cocatalyst such as $Pb_3C^+B(Ar_3F)_4$, $BAr_3^F$ or methyl alumoxane where $Ar^F$ is a fluoroaryl group is an effective catalyst for the polymerization of α-olefins such as ethylene, propylene and styrene.

Materials and Methods. All manipulations of air-sensitive materials were performed with rigorous exclusion of oxygen and moisture in flamed Schlenk-type glassware on a dual-manifold Schlenk line or interfaced to a high-vacuum line ($10^{-6}$ torr), or in a nitrogen-filled Vacuum Atmospheres glove box with a high capacity recirculator (<1 ppm $O_2$). Argon, hydrogen (Matheson, prepurified), ethylene and propylene (Matheson, polymerization grade) were purified by passage through a supported MnO oxygen-removal column and an activated Davison 4A molecular sieve column. Ether solvents were purified by distillation from Na/K alloy benzophenone ketyl. Hydrocarbon solvents (toluene and pentane) were distilled under nitrogen from Na/K alloy. All solvents for high-vacuum line manipulations were stored in vacuo over Na/K alloy in Teflon-valved bulbs. Deuterated solvents were obtained from Cambridge Isotope Laboratories (all ≧99 atom %D), were freeze-pump-thaw degassed, dried over Na/K alloy and stored in resealable flasks. Other non-halogenated solvents were dried over Na/K alloy and halogenated solvents were distilled from $P_2O_5$ and stored over activated Davison 4A molecular sieves. $C_6F_5Br$ (Aldrich) was vacuum distilled from $P_2O_5$. Styrene (Aldrich) was dried over $CaH_2$ and vacuum-transferred into a storage tube containing activated 4A molecular sieves. $TiCl_4$, $ZrCl_4$, $PhCH_2MgCl$ (1.0M in diethyl ether), BuLi (1.6M in hexanes), 2-bromo-4-methylphenol and 2,3,4,5-tetramethyl-2-cyclopentenone were purchased from Aldrich. $Ti(CH_2Ph)_4$, $Zr(CH_2Ph)_4$, $B(C_6F_5)_3$, $Ph_3C^+B(C_6F_5)_4^-$ were prepared according to literature procedures.

Physical and Analytical Measurements. NMR spectra were recorded on either Varian VXR 300 (FT 300 MHz, $^1H$; 75 MHz, $^{13}C$) or Germini-300 (FT 300 MHz, $^1H$; 75 MHz, $^{13}C$; 282 MHz, $^{19}F$) instruments. Chemical shifts for $^1H$ and $^{13}C$ spectra were referenced to internal solvent resonances and are reported relative to tetramethylsilane. $^{19}F$ NMR spectra were referenced to external $CFCl_3$. NMR experiments on air-sensitive samples were conducted in Teflon valve-sealed sample tubes (J. Young). NMR assays of polymer microstructure were conducted in $C_2D_2Cl_4$ at 120° C. Melting temperatures of polymers were measured by DSC (DSC 2920, TA Instruments, Inc.) from the second scan with a heating rate of 20° C./min. GPC analyses of polymer samples were performed on a Waters 150C GPC relative to polystyrene standards.

Synthesis of 2-Tetramethylcyclopentadienyl-4-methylphenol (TCP)$H_2$. Into a 1 L Schlenk flask were charged 50.0 g (267 mmol) of 2-bromo-4-methylphenol and 250 mL of THF, and then 350 mL of "BuLi (560 mmol, 1.6M in hexane) was added dropwise with stirring at 0° C. A white precipitate formed and the resulting mixture was allowed to warm to room temperature and stirred for another 2 h. The solution was next cooled to −78° C. and 2,3,4,5-tetramethyl-2-cyclopentenone (40.2 mL, 36.9 g, 267 mmol) was added dropwise over 30 min. The resulting solution was then allowed to warm to room temperature and stirred overnight. The reaction mixture was next treated with 20 mL of water followed by 120 mL of concentrated HCl. The organic layer was separated and treated three times with 40 mL of concentrated HCl. Volatiles were removed by rotary evaporation and the oily residue was distilled under vacuum at 150° C./15 torr to yield 28.5 g of the title ligand as a dark brown crystalline sold. Yield: 46.8% $^1H$ NMR ($C_6D_6$, 23° C.); δ 6.88 (s, 1 H, Ar), 6.78 (m, 2 H, Ar), 3.00 (s, 1 H, OH), 2.50 (q, $J_{H-H}$=6.6 Hz, 1 H, Cp—H), 2.18 (s, 3 H, Ar—$CH_3$), 1.63 (s, 3 H, Cp—$CH_3$), 1.48 (s, 3 H, Cp—$CH_3$), 1.28 (s, 3 H, Cp—$CH_3$), 1.00 (d, $J_{H-H}$=7.2 Hz, 3 H, Cp—$CH_3$). $^{13}C$ NMR ($C_6D_6$, 23° C.): δ157.11, 138.57, 132.63, 129.18, 125.40 (Ar), 109.88, 101.36, 58.37, 51.40 (Cp), 24.86 (Ar—$CH_3$), 21.00, 20.45, 12.27, 9.63 (Cp—$CH_3$). Anal. Calcd for $C_{16}H_{20}O$: C, 84.16; H, 8.83. Found: C, 84.37; H, 8.94.

Synthesis of (TCP)Ti(CH$_2$Ph)$_2$. Ti(CH$_2$Ph)$_4$ (1.01 g, 2.40 mmol), (TCP)$H_2$ (0.46 g, 2.0 mmol), and 50 mL of toluene were heated with stirring at 60°–65° C. for 30 h in the absence of light. The solvent was removed in vacuo and the black residue was extracted with 50 mL of pentane. The pentane extracts were then filtered and the solvent was removed from the filtrate under vacuum. The resulting crude product was washed with 5 mL of cold pentane and dried to produce 0.46 g of the pure product as a brown solid. Yield: 50.4% The product is very soluble in pentane. $^1H$ NMR ($C_6D_6$, 23° C.); δ 7.13 (d, $J_{H-H}$=7.5 Hz, 4 H, Ph), 7.04 (d, $J_{H-H}$=7.5 Hz, 4 H, Ph), 6.89 (d, $J_{H-H}$=8.1 Hz, 2 H, Ar), 6.83 (t, $J_{H-H}$=7.5 Hz, 2 H, Ph), 6.59 (d, $J_{H-H}$=7.5 Hz, 1 H, Ar), 2.50 (d, $J_{H-H}$=10.2 Hz, 2 H, CH$_2$Ph), 2.32 (d, $J_{H-H}$=10.2 Hz, 2 H, CH$_2$Ph), 2.11 (s, 3 H, Ar—$CH_3$), 1.90 (s, 6 H, $C_5Me_4$), 1.44 (s, 6 H, $C_5Me_4$). $^{13}C$ NMR ($C_6D_6$, 23° C.): δ 170.71, 147.87, 136.73, 130.50, 130.00, 129.76, 128.70 (Ar, Ph), 123.07, 121.18, 114.00 (Cp), 83.85 (t, $J_{C-H}$=127.5 Hz, CH$_2$Ph), 20.73 (Ar—$CH_3$), 11.49 ($C_5Me_4$). Anal. Calcd for $C_{30}H_{32}OTi$: C, 78.93; H, 7.09. Found: C, 78.67; H, 6.83.

Synthesis of (TCP)$_2$Zr. Zr(CH$_2$Ph)$_4$ (2.10 g, 4.60 mmol), (TCP)$H_2$ (0.840 g, 3.68 mmol) and 50 mL of toluene were heated with stirring at 110° C. for 12 h in the absence of light. Using the same work-up procedure as the synthesis of (TCP)Ti(CH$_2$Ph)$_2$ above, 0.35 g of the (TCP)$_2$ Zr complex was isolated as a colorless crystalline solid. Yield: 35.0%. $^1H$ NMR ($C_6D_6$, 23° C.): δ 7.07 (d, $J_{H-H}$=2.1 Hz, 2 H, Ar), 7.01 (d, $J_{H-H}$=7.8 Hz, $J_{H-H}$=2.1 Hz, 2 H, Ar), 6.73 (d, $J_{H-H}$=8.4 Hz, 2 H, Ar), 2.25 (s, 6 H, Ar—$CH_3$), 2.08 (s, 6 H, $C_5Me_4$), 1.78 (s, 6 H, $C_5Me_4$), 1.72 (s, 12 H, $C_5Me_4$). $^{13}C$ NMR ($C_6D_6$, 23° C.): δ 173.89, 138.84, 129.91, 129.24, 129.18, 126.47 (Ar), 120.14, 118.42, 117.09, 115.83 (Cp), 20.83 (Ar—$CH_3$), 11.07, 10.56, 10.00, 9.52 ($C_5Me_4$). Anal. Calcd for $C_{32}H_{36}O_2Zr$: C, 70.67; H, 6.67. Found: C, 70.49; H, 6.73.

In Situ Generation of (TCP)TiCH$_2$Ph$^+$PhCH$_2$B($C_6F_5$)$_3$. (TCP)Ti(CH$_2$Ph)$_2$ (4.6 mg, 0.010 mmol) and B($C_6F_5$)$_3$ (5.1 mg, 0.010 mmol) were loaded in the glove box into a J-Young NMR tube which was then attached to the high vacuum line. CD$_2$Cl$_2$ (0.7~1 mL) was then vacuum-transferred into this tube at −78° C. The NMR spectroscopy was carried out at −40° C. $^1H$ NMR (CD$_2$Cl$_2$, −40° C.): δ 7.81 (t, $J_{H-H}$=7.5 Hz, 1 H), 7.65 (t, $J_{H-H}$=7.5 Hz, 1 H), 7.41 (t, $J_{H-H}$=7.5 Hz, 1 H), 7.35 (t, $J_{H-H}$=7.5 Hz, 1 H), 7.23 (d, $J_{H-H}$=7.5 Hz, 1 H), 7.07 (t, $J_{H-H}$=7.5 Hz, 2 H), 6.85 (t, $J_{H-H}$=7.5 Hz, 2 H), 6.79 (t, $J_{H-H}$=7.5 Hz, 1 H), 6.64 (d, $J_{H-H}$=6.9 Hz, 2 H), 6.10 (d, $J_{H-H}$=6.9 Hz, 1 H), 3.84 (d, $J_{H-H}$=6.3 Hz, 1 H, Ti—CH$_2$Ph), 2.96 (d, $J_{H-H}$=6.3 Hz, 1 H, Ti—CH$_2$Ph), 2.71 (s, br, 2 H, B—CH$_2$Ph), 2.44 (s, 3 H, Ar—$CH_3$), 2.33 (s, 3 H, $C_5Me_4$), 2.13 (s, 3 H, $C_5Me_4$), 2.04 (s, 3 H, $C_5Me_4$), 1.57 (s, 3 H, $C_5Me_4$). A small amount of dibenzyl (δ 2.84 ppm) was also detected in the NMR reaction. $^{19}F$ NMR (CD$_2$Cl$_2$, −40° C.): δ −130.00 (s, br, 6 F, o—F), −162.30 (t, $^3J_{H-H}$=21.4 Hz, 3 F, p—F), −165.30 (s, br, 6 F, m—F).

In Situ Generation of (TCP)TiCH$_2$Ph$^+$B($C_6F_5$)$_4$. (TCP)Ti(CH$_2$Ph)$_2$ (4.6 mg, 0.010 mmol) and Ph$_3C^+$B($C_6F_5$)$_4$ (9.2 mg, 0.010 mmol) were loaded in the glove box into a J-Young NMR tube which was then attached to the high vacuum line. CD$_2$Cl$_2$ (0.7~1 mL) was then vacuum-transferred into this tube at −78° C. The NMR spectroscopy was carried out at −60° C. $^1H$ NMR (CD$_2$Cl$_2$, −60° C.): δ

7.81 (t, $J_{H-H}$=7.5 Hz, 1 H), 7.65 (t, $J_{H-H}$=7.5 Hz, 1 H), 7.43 (t, $J_{H-H}$=7.5 Hz, 1 H), 7.40–6.90 (m, obscured by superimposed signals of Ph$_3$CCH$_2$Ph), 6.09 (d, $J_{H-H}$=8.1 Hz, 1 H), 3.84 (d, $J_{H-H}$=6.3 Hz, 1 H, Ti—CH$_2$Ph), 2.96 (d, $J_{H-H}$=6.3 Hz, 1 H, Ti—CH$_2$Ph), 2.44 (s, 3 H, Ar—CH$_3$), 2.31 (s, 3 H, C$_5$Me$_4$), 2.03 (s, 3 H, C$_5$Me$_4$), 1.59 (s, 3 H, C$_5$Me$_4$). A small amount of dibenzyl (δ 2.83 ppm) was also detected in the NMR reaction $^{13}$C NMR (CD$_2$Cl$_2$, −60° C.): δ 82.56 (t, $J_{C-H}$=150.8 Hz, Ti—CH$_2$Ph). $^{19}$F NMR (CD$_2$Cl$_2$, −60° C.): δ −131.86 (s, br, 8 F, o—F), −161.08 (t, $^3J_{F-F}$=21.2 Hz, 4 F, p—F), −165.03 (s, br, 8 F, m—F).

Ethylene, Propylene and Styrene Polymerization Experiments. Ethylene, propylene and styrene polymerizations were carried out at room temperature in 250-mL flamed, round-bottom flasks equipped with magnetic stirring bars and attached to a high vacuum line. In a typical experiment, a 1:1 ratio of (TCP)Ti(CH$_2$Ph)$_2$: cocatalyst in 2 mL of toluene or 1,2-difluorobenzene (for those catalysts activated with Ph$_3$C$^+$B(C$_6$F$_5$)$_4$), freshly prepared in the glove box, was quickly injected (using a gas-tight syringe equipped with a spraying needle) into a rapidly stirred flask containing a measured quantity of dry toluene which was pre-saturated under 1.0 atm of rigorously purified ethylene or propylene. For styrene polymerization, the toluene solution contained 2.0 mL of freshly distilled styrene under 1.0 atm of Ar. After a measured time interval, the polymerization was quenched by the addition of 2% acidified methanol. The polymer was then collected by filtration, washed with methanol and dried on the high vacuum line overnight to a constant weight.

X-Ray Crystallographic Studies of (TCP)Ti(CH$_2$Ph)$_2$. Orange crystals of (TCP)Ti-(CH$_2$Ph)$_2$ were grown by slow cooling of a saturated pentane solution to −20° C. over several days. The solvent was decanted in the glove box and the crystals were quickly covered with a layer of Paratone-N oil (Exxon, dried and degassed at 120° C./10$^{-6}$ torr for 24 h). The crystals were then mounted on thin glass fibers and transferred into the cold-steam (−120° C.) of the Enraf-Nonius CAD4 diffractometer. Final cell dimensions were obtained by at least-squares fit to the automatically centered settings for 25 reflections. Intensity data were all corrected for absorption, anomalous dispersion and Lorentz and polarization effects. The space group was determined by statistical analysis of intensity distribution and successful refinement of the proposed structure. Crystallographic data are summarized in Table 1.

TABLE 1

Summary of the Crystal Structure Data for TCP)Ti(CH$_2$Ph)$_2$

| Formula | C$_{30}$H$_{32}$TiO |
|---|---|
| Formula Weight | 456.48 |
| Crystal Color, Habit | orange, platey |
| Crystal Dimensions (mm) | 0.24 × 0.15 × 0.01 |
| Crystal System | triclinic |
| α, Å | 8.324(3) |
| b, Å | 10.432(4) |
| c, Å | 14.634(4) |
| α, deg | 85.67(3) |
| β, deg | 79.23(3) |
| γ, deg | 76.64(4) |
| V, Å$^3$ | 1213.9(8) |
| Space Group | P$\bar{1}$ (#2) |
| Z | 2 |
| d (calc), g/cm$^3$ | 1.249 |
| μ, cm$^{-1}$ | 3.72 |
| Diffractometer | Enraf-Nonius, CAD4 |
| Radiation | MoK$_\alpha$(λ = 0.71069 Å) graphite monochromated |
| Temperature | −120° C. |

TABLE 1-continued

Summary of the Crystal Structure Data for TCP)Ti(CH$_2$Ph)$_2$

| Scan Type | ω–θ |
|---|---|
| 2θ Rage, deg | 2.0–45.9 |
| Intensities (unique, R$_i$) | 3634 (3358, 0.114) |
| Transmission Factor Range | 0.9543–0.9970 |
| Secondary Extinction | coefficient: 6.29514e-08 |
| Intensities > 3σ(I) | 1335 |
| No. of Parameters | 220 |
| R | 0.066 |
| Rw | 0.054 |
| Max Densities in ΔF Map, e$^-$/Å$^3$ | 0.37 |

The structure was solved by direct methods and expanded using Fourier techniques. Owing to the paucity of data, atoms C17–C30 (the benzyl groups) were refined isotopically while the remaining non-hydrogen atoms were refined anisotopically. The hydrogen atoms were included in idealized positions. The final cycle of full-matrix least-squares refinement was based on 1335 observed reflections (I>3.00 σ(I)) and 220 variable parameters. All calculations were performed using the TeXsan crystallographic software package of Molecular Structure Corporation.

Synthesis of (TCP)H$_2$, (TCP)Ti(CH$_2$Ph)$_2$ and (TCP)$_2$Zr. The "one-pot" synthesis of the 2-tetramethylcyclopentadienyl-4-methylphenolligand (TCP)H$_2$ is described below. The reaction of commercially available 2-bromo-4-methylphenol with 2 equiv of $^n$BuLi yields a dilithio salt, which is not isolated and is next reacted with 2,3,4,5-tetramethyl-2-cyclopentenone to produce the ligand (TCP)H$_2$ (obtained as a single isomer judging from the NMR) as a brown crystalline solid after hydrolysis and subsequent vacuum distillation. This approach can be compared to the conventional three-step synthesis of Me$_2$Si (C$_5$Me$_4$H)($^t$BuNH), with the attraction of the present system being the efficient synthetic procedure as well as the great potential steric and electronic flexibility introducible via modification of the aryl fragment.

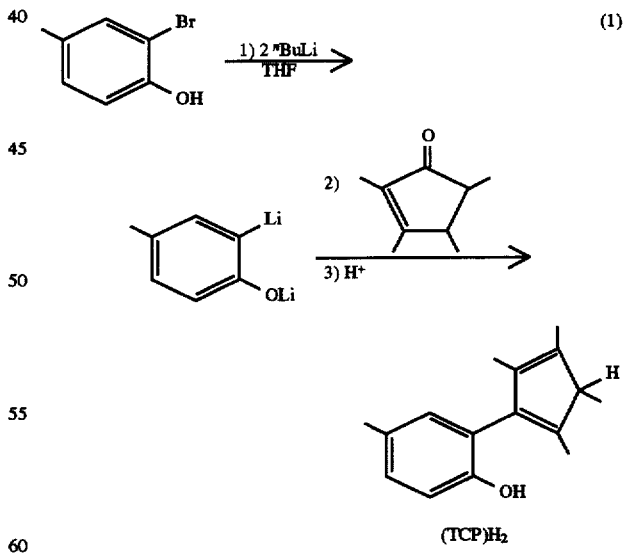

When synthesizing the corresponding group 4 metal complexes from (TCP)H$_2$, both the conventional metallation/salt elimination (double deprotonation with $^n$BuLi followed by metallation with MCl$_4$) and amine elimination approaches ((TCP)H$_2$+M(NMe2)$_4$ at 110° C. for 3 days) gave complex mixtures of unidentified products. On the other hand, the alkane elimination approach for the efficient synthesis of group 4 constrained geometry catalysts afforded the desired complex (TCP)Ti(CH$_2$Ph)$_2$ as set forth below with 50% yield. In solution at room temperature, the $^1$H NMR spectrum of (TCP)Ti(CH$_2$Ph)$_2$ reveals two magnetically equivalent benzyl groups each having diastereotopic benzylic protons at δ 2.50 and 2.32 ppm (J$_{H-H}$=10.2 Hz). Although the observation of a normal

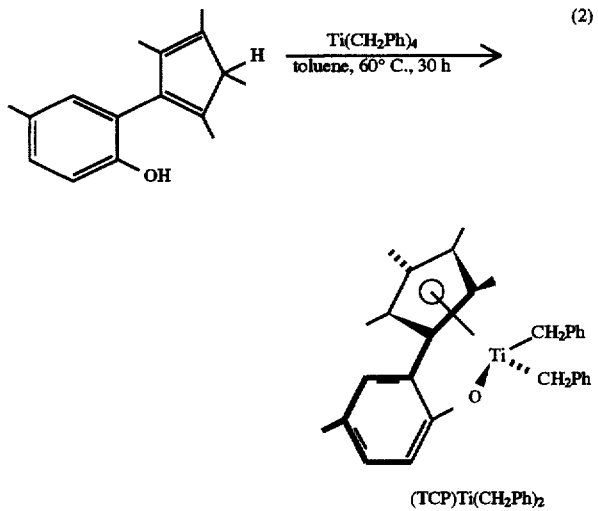

(2)

Ph iso- $^{13}$C chemical shift at δ 147.87 ppm, a CH$_2$ $^2$J$_{HH}$ value of 10.2 Hz and a CH$_2$ $^1$J$_{CH}$ value of 127.5 can be taken as evidence against significant η$^1$-benzyl bonding, the solid state structural results suggest rapid interconversion of one η$^1$- and one η$^2$ group in solution at room temperature.

The corresponding reaction of (TCP)H$_2$ with Zr(CH$_2$Ph)$_4$ under the same conditions yields a mixture of products. However, at higher reaction temperatures (110° C. for 12 h), the reaction yields a new, chiral chelated, C$_2$-symmetric zirconocene (TCP)$_2$Zr which has been characterized spectroscopically and analytically. This salt-free synthetic/ligational approach, which by design yields only the rac isomer, may offer attractive features in the stereoselective synthesis of other precursors for rac-metallocene catalysts.

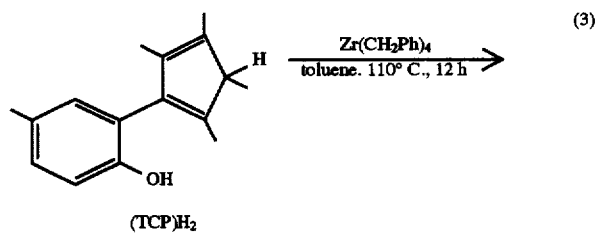

(3)

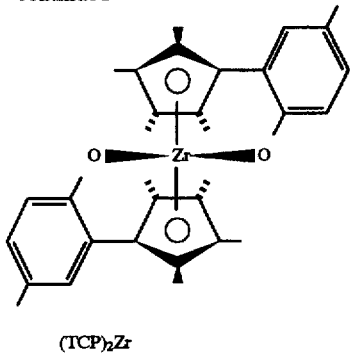

(TCP)$_2$Zr

Crystal Structure of (TCP)Ti(CH$_2$Ph)$_2$. The solid state structure of (TCP)Ti(CH$_2$Ph)$_2$ as derived from single X-ray diffraction is shown in FIG. 1 and important bond distances and angles are summarized in Table 2. The geometry around Ti is a slightly distorted tetrahedral with a Cp(centroid)-Ti—O angle of 107.7(2)° and a C17-Ti-C24 angle of 101.1(4)°. This acute Cp(centroid)-Ti-O angle is nearly identical to that of Cp-Ti-N angle in Me$_2$Si(Me$_4$C$_5$)('BuN)TiCl$_2$ (107.6) indicating similar sterically open features for both complexes as catalyst precursors. The Ti-C$_{ring}$(av) distance of 2.36(1) Å is probably slightly longer than the corresponding distance in Me$_2$Si(Me$_4$C$_5$)('BuN)TiCl$_2$ (2.340(5) Å).$^{30}$ The (phenyl)C10-Cl(ring) vector in (TCP)Ti(CH$_2$Ph)$_2$ is bent 15(1)° from the Me$_4$Cp ring mean-square plane and the phenyl plane-Me$_4$Cp plane dihedral angle is 81(1)°. The Ti-O bond length in (TCP)Ti(CH$_2$Ph)$_2$ (1.851(7) Å) is comparable to those reported for bent metallocene Ti$^{IV}$ and Ti$^{III}$ alkoxide complexes, such as Cp$_2$Ti(OCH=CH$_2$)$_2$ (1.903 ((TCP)Ti(CH$_2$Ph)$_2$) (1.903(2) Å), Cp$_2$Ti(OC$_2$H$_5$)Cl (1.855 (2) Å), Cp$_2$TiO(2,6-Me$_2$C$_6$H$_3$) (1.892(2) Å), [C$_5$H$_4$(CH$_2$)$_3$O]TiCl$_2$ (1.762(2) Å) and [C$_5$Me$_4$(CH$_2$)$_3$O]TiCl$_2$ (1.767(1) Å), where a partial Ti-O double bond character involving oxygen π-donation to the metal in addition to the σ-interaction is associated with short Ti-O bond lengths. On the other hand, the present Ti-O-C15 angle (126.6(6)°) is somewhat smaller than typical Ti-O-C angles as in the above examples (~140°) where Ti-O multiple bonding is assumed operative, reflecting the great steric strain in (TCP)Ti(CH$_2$Ph)$_2$, also evidenced by the 15° bend of the (phenyl) C10-Cl(ring) vector from the Me$_4$Cp ring mean-square plane.

The two benzyl ligands in complex (TCP)Ti(CH$_2$Ph)$_2$ are not equivalent in the solid state, with one engaging in normal η$^1$-bonding (Ti-C24=2.13(1)Å; ∠Ti-C24–C25=127.2(7)°) and the other in partial η$^2$-bonding with Ti-C17 and Ti-C$_{ipso}$ (C18) distances of 2.121(10) and 2.92(1) Å, respectively, and a Ti-C17-C18 angle of 106.7(7)°(FIG. 1).

TABLE 2

Selected Bond Distances (Å) and Angles (deg) for (TCP)Ti(CH$_2$Ph)$_2$

| Bond Distances | | | |
|---|---|---|---|
| Ti—O | 1.851(7) | Ti—C1 | 2.33(1) |
| Ti—C2 | 2.36(1) | Ti—C3 | 2.39(1) |
| Ti—C4 | 2.37(1) | Ti—C5 | 2.35(1) |
| Ti—C17 | 2.121(10) | Ti—C24 | 2.13(1) |
| Ti—C18 | 2.92(1) | C24—C25 | 1.50(1) |
| O—C15 | 1.36(1) | C17—C18 | 1.49(1) |

TABLE 2-continued

Selected Bond Distances (Å) and Angles (deg) for (TCP)Ti(CH$_2$Ph)$_2$

| Bond Angles | | | |
|---|---|---|---|
| O—Ti—C17 | 104.5(4) | O—Ti—C24 | 108.0(4) |
| Ti—O—C15 | 126.6(6) | Ti—C17—C18 | 106.7(7) |
| Ti—C24—C25 | 127.2(7) | O—C15—C10 | 116.6(10) |
| O—C15—C14 | 124(1) | C1—C10—C15 | 112.6(10) |
| C1—C10—C11 | 128(1) | C17—Ti—C24 | 101.1(4) |
| Cp(centroid)-Ti—O | 107.7(2) | | |

Reaction Chemistry of (TCP)Ti(CH$_2$Ph)$_2$ with B(C$_6$F$_5$)$_3$ and Ph$_3$C$^+$B(C$_6$F$_5$)$_4^-$. The reaction of bis-Cp-type metallocene dibenzyls with B(C$_6$F$_5$)$_3$ and Ph$_3$C$^+$B(C$_6$F$_5$)$_4^-$ often generates the corresponding cationic complexes with η$^2$-bonding of the remaining benzyl group to the electrophilic metal center. In contrast, the reaction of the Me$_2$Si (Me$_4$C$_5$)("BuN)M(CH$_2$Ph)$_2$ complexes with B(C$_6$F$_5$)$_3$ and Ph$_3$ C$^+$B(C$_6$F$_5$)$_4^-$ follows a different course. While low-temperature NMR-scale reactions of Me$_2$Si(Me$_4$C$_5$) ("BuN) M(CH$_2$Ph)$_2$ complexes with B(C$_6$F$_5$)$_3$ and Ph$_3$C$^+$B(C$_6$F$_5$)$_4^-$ in CD$_2$Cl$_2$ indicate the formation of cationic monobenzyl species, preparative scale reactions at higher temperature afford C—H activation products, i.e., intramolecularly ring-metallated η$^1$, η$^6$ -fulvene-type complexes.

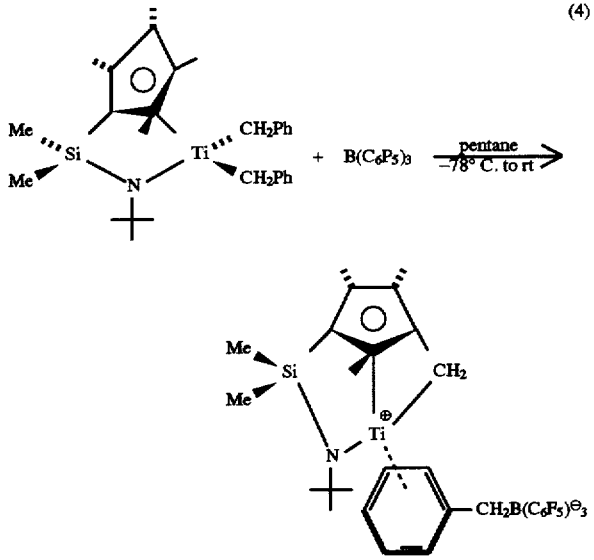

(4)

Likewise, the low-temperature NMR-scale reactions of (TCP)Ti(CH$_2$Ph)$_2$ with B(C$_6$F$_5$)$_3$ and Ph3C$^+$B(C$_6$F$_5$)$_4^-$ in CD$_2$Cl$_2$ clearly indicate the formation of the corresponding cationic monobenzyl species (TCP)TiCH$_2$Ph$^+$PhCH$_2$B (C$_6$F$_5$)$_3^-$ and (TCP)TiCH$_2$Ph$^+$B(C$_6$F$_5$)$_4^-$, respectively, with identical cation structures based upon the NMR analyses. The Ti-CH$_2$Ph $^1$H NMR signals of (TCP)TiCH$_2$Ph$^+$B(C$_6$F$_5$)$_4^-$, are observed at δ 3.84 (d, J$_{H-H}$= 6.3 Hz) and 2.96

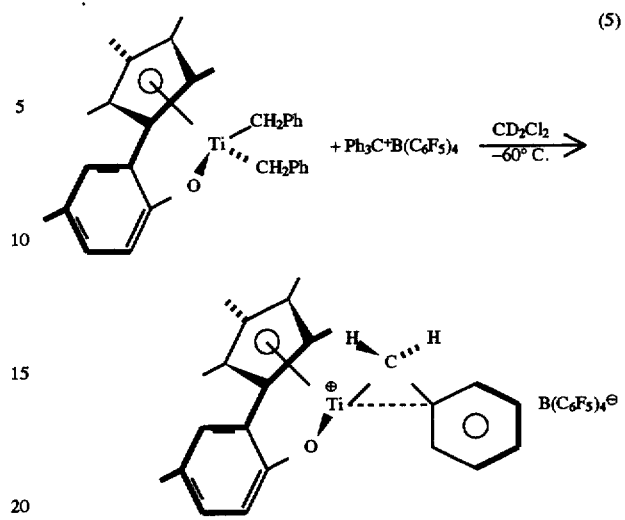

(5)

(d, J$_{H-H}$=6.3 Hz) (CD$_2$Cl$_2$, –60° C.), which is 1.34 and 0.64 ppm down-field shifted, respectively, from the benzyl resonances of neutral precursor (TCP)Ti(CH$_2$Ph)$_2$ δ 2.50 (d, J$_{H-H}$=10.2 Hz) (C$_6$D$_6$, 23° C.) as a consequence of cation formation. η$^2$-coordination of the benzyl ligand in the cationic complex is evidenced by a reduction of the value of $^2$J$_{H-H}$ for the diastereotopic CH$_2$Ph protons from 10.2 to 6.3 Hz, a high-field shifted Ti-$^{13}$CH$_2$Ph signal and a large CH$_2^1$JCH value. However, despite the clean NMR-scale reactions at low temperatures and unlike the case of the constrained geometry monobenzyls, preparative scale reactions at higher temperatures are accompanied by extensive decomposition and isolation of the cationic complex could not be achieved in this case.

α-Olefin Polymerization Studies. Table 3 summarizes ethylene, propylene, and styrene polymerization activities of (TCP) Ti(CH$_2$Ph)$_2$ upon activation with B(C$_6$F$_5$)$_3$ and Ph$_3$C$^+$B(C$_6$F$_5$)$_4^-$ as well as the properties of the resulting polymers. (TCP)Ti(CH$_2$Ph)$_2$ when activated with Ph$_3$C$^+$B (C$_6$F$_5$)$_4^-$ is a highly active catalyst for ethylene, propylene, and styrene polymerization, producing high molecular weight (>10$^6$) polyethylenes with high melting transition temperatures (T=142EC), as well as atactic polypropylene and polystyrene. The open nature of the catalytic site can be associated with the low degree of polymerization stereocontrol, and the homopoly α-olefin products are generally atactic, similar to the performance of group 4 amido-based constrained geometry catalysts. The broad polydispersities of the polyethylene products may be associated with the rapid decomposition of the cationic species at room temperature (possibly with the formation of η$^1$, η$^6$ "tuck-in" cations) or slow initiation with respect to the faxt propagation, and significant inhomogeneity during the course of the catalytic reaction under the present ethylene polymerization conditions. In contrast, propylene polymerization mediated by (TCP)Ti(CH$_2$Ph)$_2$ activated with Ph$_3$C$^+$ B(C$_6$F$_5$)$_4^-$ is both very rapid and produces a polymer having narrow polydispersity, which can be attributed to the structurally open nature of the cationic metal coordination sphere (catalytic activity is not affected by the steric encumbrance of monomer) and apparently greater stabilization of the catalytic sites in the presence of propylene. The substantial activity difference of identical cations having different counteranions (entry 1 vs 2) further demonstrates the significant influence of the anion identity on catalytic activity as previously shown in detail by us and others.

TABLE 3

| entry | cocatalyst | conditions | monomer[a] | polymer yield (g) | activity[b] | $M_w$[c] | $M_w/M_n$ | remarks |
|---|---|---|---|---|---|---|---|---|
| 1. | $B(C_6F_5)_3$ | 15 μmol catalyst 100 mL toluene, 30 min | ethylene | 0.11 | $1.47 \times 10^4$ | $1.27 \times 10^6$ | >10 | $T_m = 142.5°$ C. |
| 2. | $Ph_3C^+B(C_6F_5)_4^-$ | 15 μmol catalyst 100 mL toluene, 1 min | ethylene | 0.52 | $2.10 \times 10^6$ | $1.14 \times 10^6$ | >10 | $T_m = 142.4°$ C. |
| 3. | $Ph_3C^+B(C_6F_5)_4^-$ | 20 μmol catalyst 50 mL toluene, 5 min | propylene | 6.37 | $3.82 \times 10^6$ | $2.36 \times 10^4$ | 1.85 | [mm] = 0.224 [mr] = 0.512 [rr] = 0.264 |
| 4. | $Ph_3C^+B(C_6F_5)_4^-$ | 25 μmol catalyst 5 mL toluene, 5 min | styrene | 1.57 | $4.33 \times 10^7$ | $8.00 \times 10^3$ | 3.32 | atactic |

[a]Carried out at 25° C., 1 atm ethylene, 1 atm propylene and 17.4 mmol styrene.
[b]Activities in units of g polymer (mole catalyst-atm-h), except entry 4 in unit of g polystyrene (mole catalyst-mole styrene-h).
[c]GPC relative to polystyrene standards.

In summary, a novel phenolic bifunctional mono-Cp "constrained geometry" ligand framework and the Ti and Zr complexes thereof have been designed and synthesized by "one-pot"/one-step syntheses. The solid state structure, activation chemistry, and performance for olefin polymerization of the titanium complex are described. The results considerably expand what is known about "constrained geometry" catalyst design and the consequent olefin polymerization performance.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or maerial to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

Various features of the invention are set forth in the following claims.

We claim:

1. A catalytic complex of the formula:

$(Ar'R_4)(O)(Ar''R'_4)M(CH_2Ph)_2$ where

Ar' is a phenyl or naphthyl group;

Ar" is a cyclopentadienyl or indenyl group;

R, R' is each H, alkyl (C≦10) or a mixture thereof; and

M is Ti, Zr, or Hf.

2. A method of preparing a catalyst including the step of adding 2-tetra methylcyclopentadienyl-4-methyl phenol to $Ti(CH_2Ph)_4$.

3. The method of claim 2, further including a last step of adding $Ph_3C^+B(Ar_3^F)_4^-$, $BAr_3^F$, or methyl alumoxane, where $Ar^F$ is a fluoroaryl group.

4. A method of polymerizing an olefin comprising the step of adding a catalyst to said olefin, said catalyst including the combination of $(TCP)M(CH_2Ph)_2$, where TCP=2-tetramethylcyclopentadienyl-4-methyl phenolate; and $Ph_3C^+B(C_6F_5)_4^-$.

5. The method of claim 4, wherein the polymerization is carried out at 25° C.

6. The method of claim 4, wherein said olefin is an α-olefin.

7. The method of claim 4, wherein said olefin is selected from the group consisting of ethylene, propylene and styrene.

8. A catalytic complex of the formula: $(TCP)M(CH_2Ph_2)$ where

TCP is 2-tetramethylcyclopentadienyl-4-methyl phenolate; and

M is Ti, Zr, or Hf.

* * * * *